United States Patent [19]

Imai et al.

[11] 4,144,254

[45] Mar. 13, 1979

[54] PROCESS FOR THE PURIFICATION OF STEROIDS

[75] Inventors: Haruo Imai, Yokohama; Tadashi Oohama, Tokyo; Ryozo Yamaguchi; Kunihiro Ninomiya, both of Yokohama, all of Japan

[73] Assignee: Mitsubishi Chemical Industries Limited, Tokyo, Japan

[21] Appl. No.: 855,684

[22] Filed: Nov. 29, 1977

[30] Foreign Application Priority Data

Dec. 7, 1976 [JP] Japan .................................. 51-146833

[51] Int. Cl.$^2$ .............................................. C07J 7/00
[52] U.S. Cl. ............................... 260/397.4; 260/397.3
[58] Field of Search ................... 260/397.3; 261/397.4

[56] References Cited

FOREIGN PATENT DOCUMENTS 528609 7/1956 Canada .................................. 260/397.3
544544 8/1957 Canada .................................. 260/397.3

*Primary Examiner*—Elbert L. Roberts
*Assistant Examiner*—Robert C. Whittenbaugh
*Attorney, Agent, or Firm*—Oblon, Fisher, Spivak, McClelland & Maier

[57] ABSTRACT

19-Norethisterone or 19-norandrost-4-ene-3,17-dione is purified by passing its solution in an aromatic hydrocarbon, an alkyl halide or an ester of acetic acid through a column packed with basic alumina and then crystallizing it.

22 Claims, No Drawings

PROCESS FOR THE PURIFICATION OF STEROIDS

BACKGROUND OF THE INVENTION

1. Field of the invention

This invention relates to a process for the purification of steroids such as 19-norethisterone and 19-norandrost-4-ene-3,17-dione.

More particularly, this invention relates to a process for purifying crude 19-norandrost-4-ene-3,17-dione or 19-norethisterone resulting from ethynylation of 19-norandrost-4-ene-3,17-dione so as to free it from such impurities as colored substances, high molecular weight substances, ethynylestradiol, estrone and the like present in the crude product.

2. Description of the Prior Art 19-norandrost-4-ene-3,17-dione is useful as an intermediate in the preparation of 19-norethisterone.

19-norethisterone is a medicament administered to a woman over a long period of time so that it has severe restrictions regarding purity, color, the number and contents of contaminants, etc. For example, according to U.S. Pharm. XIX, 19-norethisterone is required to have a purity in the range of 97.0% to 102.0% and to be white or milk white in color and the number of contaminants must be not more than three, each contaminant being present in a proportion of not more than 1%.

The crude 19-norethisterone contains as a contaminant ethynylestradiol which possesses a ovarian hormonal activity and the incorporation of which, therefore, offers a pharmacological and operation-environmental problem.

The commercial purification of 19-norethisterone has heretofore been accomplished by a relatively complicated process comprising stirring it in a reactor together with an adsorbent such as activated carbon, alumina, etc. followed by filtration and repeated crystallization. However, the recovery of pure product attained according to this process is low and it is hard to say that this process is well suited for the processing of large amounts of 19-norethisterone.

The crude 19-norethisterone resulting from the ethynylation of 19-norandrost-4-ene-3,17-dione also contains a considerably wide variety of impurities, which are difficult to be removed by means of repeated crystallization from various solvents. Moreover, if ethynylestradiol and similar contaminants are to be removed completely, the recovery of pure 19-norethisterone will be so low as to be inadequate for commercial-scale purification.

The use of conventional adsorbents such as activated carbon, silica gel, ion-exchange resins and the like enables such contaminants as colored substances, polar substances, high polymers, etc. to be removed appreciably, but those substances having rather small polarity do not tend to be removed with such an absorbent.

Among these absorbents, silica gel, neutral or acidic alumina, basic alumina calcined at a relatively low temperature, activated carbon and the like can be used to remove ethynylestradiol to some extent, but suffer from a disadvantage that complete removal of ethynylestradiol is attained only at the cost of a decreasing recovery of the desired 19-norethisterone.

Basic ion-exchange resins permit selective removal of ethynylestradiol, but they also involve a disadvantage that the other contaminants are scarcely removed therewith.

SUMMARY OF THE INVENTION

Accordingly, it is an object of this invention to provide a simple, commercially applicable process for removing impurities from crude 19-norethisterone or its starting 19-norandrost-4-ene-3,17-dione to obtain a high recovery of purified 19-norethisterone or 19-norandrost-4-ene-3,17-dione which is entirely freed from those compounds having ovarian hormonal activity, for example, ethynylestradiol or estrone.

Briefly, this and other objects of this invention, as will hereinafter be made clear from the ensuing discussion, have been attained by a process which comprises:
(a) dissolving crude 19-norandrost-4-ene-3,17-dione or 19-norethisterone in at least one solvent selected from the group consisting of an aromatic hydrocarbon optionally having one or more side chains, an alkyl halide and an ester of acetic acid,
(b) passing the resulting solution through a column packed with basic alumina, and
(c) crystallizing pure 19-norandrost-4-ene-3,17-dione or 19-norethisterone from the alumina-treated solution using as the crystallization solvent at least one member selected from the group consisting of an aromatic hydrocarbon optionally having one or more side chains, an alkyl halide, a ketone, an alcohol and an aliphatic hydrocarbon.

The solvents to be used for the dissolution of crude 19-norandrost-4-ene-3,17-dione or 19-norethisterone derived from the ethynylation of 19-norandrost-4-ene-3,17-dione include aromatic hydrocarbons optionally having one or more side chains and typically having 6 to 20 carbon atoms, such as benzene, toluene, xylene, ethylbenzene and the like; alkyl halides typically having 1 to 10 carbon atoms and optionally containing a double bond, such as carbon tetrachloride, chloroform, methylene dichloride, 1,2-dichloroethane, 1,1-dichloroethane, 1,1,1-trichloroethane, 1,1,2-trichloroethane, 1,1,2-trichloroethylene 1,1,2,2,-tetrachloroethane and the like; and esters of acetic acid typically having 3 to 10 carbon atoms such as ethyl acetate, propyl acetate, butyl acetate and the like. A mixture of two or more these solvents, for example, toluene-chloroform or toluene-methylene dichloride may be used similarly for the dissolution of crude 19-norandrost-4-ene-3,17-dione or 19-norethisterone. From the standpoints of boiling temperature, stability and efficiency of purification, preferred solvents for 19-norethisterone are aromatic hydrocarbons having one or more side chains such as toluene, xylene and ethylbenzene; 1,2-dichloroethane, 1,1,2-trichloroethylene, toluene-chloroform and toluene-methylene dichloride. Similarly, preferred solvents for 19-norandrost-4-ene-3,17-dione are benzene, toluene, xylene, ethylbenzene, 1,2-dichloroethane, 1,1,2-trichloroethane, 1,1,2-trichloroethylene, 1,1,2,2-tetrachloroethane and butyl acetate.

Among these, the most preferred solvent for 19-norethisterone is 1,2-dichloroethane. Similarly, the most preferred solvent for 19-norandrost-4-ene-3,17-dione is benzene.

It is desirable to dissolve 19-norandrost-4-ene-3,17-dione or 19-norethisterone in the solvent at a concentration that is close to the solubility of 19-norandrost-4-ene-3,17-dione or 19-norethisterone at the temperature at which the subsequent basic alumina treatment is carried out and that does not cause 19-norandrost-4-ene-3,17-dione or 19-norethisterone to precipitate.

Suitable basic alumina is those class of alumina containing a relatively large amount of sodium oxide (e.g., more than about 0.2%) and calcined at a relatively high temperature (e.g., above about 400° C., preferably 500° C.). The particle size of the basic alumina is in the range of 10 to 100 mesh, preferably in the range of 20 to 80 mesh, and more preferably in the range of 30 to 60 mesh. The basic alumina treatment is usually carried out at a temperature up to 70° C., preferably in the range of 10 to 30° C.

Preferably the basic alumina treatment is conducted at a linear velocity of not greater than 5 m/hr, more preferably not greater than 3 m/hr.

The basic alumina treatment permits undesirable impurities such as colored substances, high polymers, ethynylestradiol, estrone, etc. to be removed.

Subsequently pure 19-norandrost-4-ene-3,17-dione or 19-norethisterone is crystallized from the alumina-treated solution using as the crystallization solvent at least one member selected from the group consisting of an aromatic hydrocarbon optionally having one or more side chains, an alkyl halide, a ketone, an alcohol and an aliphatic hydrocarbon.

In practice, the crystallization of 19-norandrost-4-ene-3,17-dione or 19-norethisterone may be accomplished, for example, by any of the following procedures:

(A) The alumina-treated solution is sufficiently cooled to precipitate 19-norandrost-4-ene-3,17-dione or 19-norethisterone.

(B) The alumina-treated solution is sufficiently concentrated to precipitate 19-norandrost-4-ene-3,17-dione or 19-norethisterone.

(C) The alumina-treated solution is either concentrated sufficiently or evaporated to dryness, whereupon at least one crystallization solvent selected from the group consisting of an aromatic hydrocarbon optionally having one or more side chains, an alkyl halide, a ketone, an alcohol and an aliphatic hydrocarbon is added anew and the mixture is first heated to dissolve the 19-norandrost-4-ene-3,17-dione or 19-norethisterone crystals in the crystallization solvent and then cooled to precipitate them.

Thus, when an aromatic hydrocarbon optionally having one or more side chains or an alkyl halide is employed as the solvent for use in dissolving the crude 19-norandrost-4-ene-3,17-dione or 19-norethisterone and the crystallization of pure 19-norandrost-4-ene-3,17-dione or 19-norethisterone is accomplished by means of cooling or concentration of the solvent, it is not always necessary to add a fresh solvent in the crystallization step.

The above-mentioned crystallization solvents include aromatic hydrocarbons optionally having one or more side chains typically having 6 to 20 carbon atoms, such as benzene, toluene, xylene, ethylbenzene and the like; alkyl halides having typically 1 to 10 carbon atoms and optionally containing a double bond, such as carbon tetrachloride, chloroform, methylene dichloride, 1,2-dichloroethane, 1,1-dichloroethane, 1,1,1-trichloroethane, 1,1,2-trichloroethane, 1,1,2-trichloroethylene, 1,1,2,2-tetrachloroethane and the like; ketones having typically 3 to 10 carbon atoms such as methyl isobutyl ketone, methyl ethyl ketone, acetone and the like; alcohols having typically 1 to 10 carbon atoms such as isopropyl alcohol and the like; and an aliphatic hydrocarbons having typically 5 to 10 carbon atoms such as n-hexane, n-heptane, n-octane, n-decane and the like.

Among these, preferred for 19-norethisterone are side chain-containing aromatic hydrocarbons such as toluene, alkyl halides such as 1,1,2-trichloroethylene and ketones such as methyl isobutyl ketone. Similarly, preferred for 19-norandrost-4-ene-3,17-dione are benzene, side chain-containing aromatic hydrocarbons such as toluene, alkyl halides such as 1,1,2-trichloroethylene, ketones such as methyl isobutyl ketone and aliphatic hydrocarbons such as n-octane.

The crystallized 19-norandrost-4-ene-3,17-dione or 19-norethisterone is then filtered off and dried.

In accordance with the process of this invention, 19-norandrost-4-ene-3,17-dione or 19-norethisterone which fully meets the requirements for purity can be obtained in high yield by the simple procedures as mentioned above. Having generally described this invention, a more complete understanding can be obtained by comparative examples and examples which are provided herein for purposes of illustration only and are not intended to be limiting in any matter.

In the following examples, the purities of the raw and purified 19-norandrost-4-ene-3,17-dione or 19-norethisterone are all determined gas-chromatographically using androsta-1,4-diene-3,17-dione as the standard sample and involve possible errors of ± 1%.

The assay of any contaminant contained in 19-norandrost-4-ene-3,17-dione or 19-norethisterone is effected by means of thin layer chromatography (hereinafter abbreviated as TLC) in the following way:

A solution of a given sample in chloroform at a concentration of 10 mg/ml is spotted with a microsyringe on a commercially available TLC plate transversely at regular intervals at 2 cm from one end of the plate. The plate is then developed in a developing column containing 300 ml of a 95/5 mixture of chloroform/methyl alcohol. When the developing solvent rises to 2 cm from the upper end of the plate, the plate is drawn upwardly out of the column, dried and then sprayed with a 1/3 mixture of sulfuric acid/methyl alcohol. After drying at 105° C. for 5 minutes, the color development appearance is inspected visually under irradiation with longer wavelength UV rays.

EXAMPLE 1

A water-jacketed glass column of 2.7 cm inner diameter is packed with a suspension of 50.0 g of basic alumina (sold by Shokubai Kasei Kogyo Co. Ltd. under trade name of ACBR-3, calcined at a temperature above 500° C. and pulverized to about 50 mesh) in 100 ml of 1,2-dichloroethane (to a depth of 13.0 cm) and water is passed through the jacket so as to set the temperature at 20° C. In 1400 ml of 1,2-dichloroethane, 20.00 g of crude 19-norethisterone of 91.8% purity which results from ethynylation of 19-norandrost-4-ene-3,17-dione and which contains 1.7% ethynylestradiol in addition to other impurities is dissolved at 20° C. and the resulting solution is introduced on the top of the column at a linear velocity of 2 m/hr using a feed pump. The 1,2-dichloroethane solution passed through the alumina is received in an Erlenmeyer flask. After the solution of 19-norethisterone in 1,2-dichloroethan has been passed, 500 ml of 1,2-dichloroethane is further passed through the alumina to wash it. The two liquids are combined and concentrated to dryness at reduced pressure with 1,2-dichloroethane being distilled off.

The residue in 190 ml of toluene is heated in a stream of nitrogen to dissolve it and then allowed to cool. Thus 17.85 g of white crystals are obtained. These crystals are of 97.8% purity and completely free from ethynylestradiol and, according to TLC, contain only two contaminants each in an amount of not more than 1%, so they pass U.S. Pharm. XIX easily. The recovery of 19-norethisterone in this procedure is 95.1%.

EXAMPLE 2

A column similar to that used in Example 1 is prepared and warm water of 50° C. is passed through the jacket. In 2.8 l of toluene, 20.00 g of the same crude 19-norethisterone as in Example 1 is dissolved at 50° C. and the resulting solution is introduced on the top of the column at a linear velocity of 3 m/hr. The toluene solution running out through the bottom of the column is received in an Erlenmeyer flask. After the solution of 19-norethisterone in toluene has been passed through the alumina, 500 ml of toluene is further passed therethrough to wash the alumina. The combined two liquids are concentrated to 200 ml at reduced pressure with toluene being distilled off, and the precipitated crystals are filtered off. These crystals (17.43 g) are white, of 98.2% purity and completely free from ethynylestradiol and, according to TLC, contain only two impurities each in an amount of not more than 1%. Therefore, they easily pass U.S. Pharm. XIX. The recovery of 19-norethisteron attained in this procedure is 93.2%.

EXAMPLE 3

A column similar to that used in Example 1 is prepared and warm water is passed through the jacket so as to set the temperature at 30° C. In 1.5 l of 4:1 toluene-chloroform 15.00 g of the same crude 19-norethisterone as in Example 1 is dissolved at 30° C., and the resulting solution is introduced on the top of the column at a linear velocity of 2 m/hr. The toluene-chloroform solution running out through the bottom of the column is received in an Erlenmeyer flask. After the solution of 19-norethisterone has been passed, 500 ml of toluene-chloroform is further passed through the alumina to wash it. The two liquids are combined and concentrated to 150 ml at reduced pressure with toluene-chloroform being distilled off. The precipitated crystals are filtered off. These crystals (13.29 g) are white, of 97.9% purity and completely free from ethynylestradiol and, according to TLC, contain only two contaminants each in an amount of not more than 1%. Accordingly, they easily pass U.S. Pharm. XIX. This procedure attains 94.5% recovery of 19-norethisterone.

Comparative Example 1

This comparison illustrates a lower purification efficiency with neutral alumina.

A column similar to that used in Example 1 is packed with a suspension of 50.0 g of neutral alumina (Neobead manufactured by Mizusawa Kagaku Kogyo Co. Ltd.) in 100 ml of 1,2-dichloroethane (to a depth of 12.5 cm) and water is passed through the jacket so as to set the temperature at 20° C. A solution of 20.0 g of the same crude 19-norethisterone as in Example 1 dissolved in 1400 ml of 1,2-dichloroethane at 20° C. is introduced on the top of the column at a linear velocity of 2 m/hr using a feed pump.

The effluent is worked up in the same manner as in Example 1 to yield 18.19 g of pale milk white crystals. These crystals are of 96.2% purity and according to TLC, approximately 0.1% ethynylestradiol and five other contaminants are detected so that they do not pass U.S. Pharm. XIX. This procedure attains 95.3% recovery of 19-norethisterone.

Comparative Example 2

This comparison shows the results of small-scale experiments conducted for the purpose of making a comparison of various carriers in their purification capacity.

A glass column of 13 mm inner diameter is packed with 2.0 g of the carrier indicated in Table 1 below, and a solution of the same crude 19-norethisterone as in Example 1 in 1,2-dichloroethane which contains 1 g of 19-norethisterone for each 140 ml amount of 1,2-dichloroethane is introduced on the top of the column at a linear velocity of 2 m/hr. The solution running out through the bottom of the column is received in 10 ml portions each in a measuring cylinder. Each fraction is concentrated to dryness at reduced pressure and spotted on a TLC plate from a solution of a certain concentration. A 0.1% solution of ethynylestradiol is also spotted in alignment with the sample spot on the TLC plate. After development with the foregoing developing solvent, the plate is sprayed with phosphomolybdic acid/sulfuric acid instead of sulfuric acid/methanol and heated at 105° C. for 5 minutes to cause color development for comparison. Among these fractions, the fraction at which the spot having the same Rf value as that of ethynylestradiol becomes deeper than the spot of standard 0.1% spot is detected. Then the total weight of 19-norethisterone eluted from the column before the detected fraction is divided by the weight of the carrier. With the thus calculated value, the ability to remove ethynylestradiol is compared. The results are summarized in Table 1 below.

Table 1

| Adsorbent | Weight of adsorbent (g) / Weight of 19-norethisterone (g) |
| --- | --- |
| Acidic alumina | 5.5 |
| Neutral alumina | 5.9 |
| Basic alumina A* | 2.2 |
| Basic alumina B* | 9.5 |
| Silica gel | >20 |

*Basic alumina A is for use as a catalyst support and Basic alumina B is for use as an adsorbent. The calcination temperature of the former is about 200° C. higher than that of the latter.

EXAMPLE 4

A water-jacketed glass column of 2.7 cm inner diameter is packed with a suspension of 25.0 g of basic alumina the same as that of Example 1 in 100 ml of benzene and water is passed through the jacket so as to set the temperature at 20° C. In 300 ml of benzene, 100 g of 19-norandrost-4-ene-3,17-dione of 89.2% purity containing 0.8% of estrone is dissolved at 20° C. and the resulting solution is introduced on the top of the column at a linear velocity of 2 m/hr. The benzene solution passed through the alumina is received in an Erlenmeyer flask. After the solution of 19-norandrost-4-ene-3,17-dione in benzene has been passed, 100 ml of benzene is further passed through the alumina to wash it. The two liquids are combined and concentrated to 40 ml at reduced pressure with benzene being distilled off. To the residue is added 360 ml of n-octane to yield 88.5 g of white crystals having a 97.2% purity. The recovery of 19-norandrost-4-ene-3,17-dione is 96.4%. Estrone is not detected gas-chromatographically.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A process for the purification of 19-norandrost-4-ene-3,17-dione or 19-norethisterone which comprises the steps of:
   (a) dissolving crude 19-norandrost-4-ene-3,17-dione or 19-norethisterone in at least one solvent selected from the group consisting of an aromatic hydrocarbon optionally having one or more alkyl side chains and having from 6 to 20 carbon atoms, an alkyl halide having from 1–10 carbon atoms and an alkyl ester of acetic acid having from 3 to 10 carbon atoms;
   (b) passing the resulting solution in its entirety through a column packed with basic alumina and collecting the total effluent as a single fraction; and
   (c) crystallizing pure 19-norandrost-4-ene-3,17-dione or 19-norethisterone from the alumina-treated solution using as the crystallization solvent at least one member selected from the group consisting of an aromatic hydrocarbon optionally having one or more alkyl side chains and having from 6 to 20 carbon atoms, an alkyl halide having from 1 to 10 carbon atoms, a ketone having from 3 to 10 carbon atoms, an alkanol having from 1 to 10 carbon atoms and an alkane having from 5 to 10 carbon atoms.

2. The process of claim 1, wherein said crude 19-norethisterone is prepared by:
   ethynylating 19-norandrost-4-ene-3,17-dione.

3. The process of claim 1, wherein said solvent in step (a) is selected from the group consisting of benzene, toluene, xylene, ethylbenzene, carbon tetrachloride, chloroform, methylene dichloride, 1,2-dichloroethane, 1,1-dichloroethane, 1,1,1-trichloroethane, 1,1,2-trichloroethane, 1,1,2-trichloroethylene, 1,1,2,2-tetrachloroethane, ethyl acetate, propyl acetate and butyl acetate.

4. The process of claim 1, wherein in said step (a), said crude 19-norethisterone is dissolved in at least one solvent selected from the group consisting of toluene, xylene, ethylbenzene, 1,2-dichloroethane, 1,1,2-trichloroethylene, toluene-chloroform and toluene-methylene dichloride.

5. The process of claim 4, wherein said solvent is 1,2-dichloroethane.

6. The process of claim 1, wherein said step (a), said crude 19-norandrost-4-ene-3,17-dione is dissolved in at least one solvent selected from the group consisting of benzene, toluene, xylene, ethylbenzene, 1,2-dichloroethane, 1,1,2-trichloroethane, 1,1,2-trichloroethylene, 1,1,2,2-tetrachloroethane and butyl acetate.

7. The process of claim 6, wherein said solvent is benzene.

8. The process of claim 1, wherein said step (c) is accomplished by sufficiently cooling said alumina-treated solution to precipitate said pure 19-norandrost-4-ene-3,17-dione or 19-norethisterone.

9. The process of claim 1, wherein said step (c) is accomplished by sufficiently concentrating said alumina-treated solution to precipitate said pure 19-norandrost-4-ene-3,17-dione or 19-norethisterone.

10. The process of claim 1, wherein said step (c) is accomplished by partially or completely evaporating the solvent from said alumina-treated solution, adding said crystallization solvent, heating to achieve dissolution, and cooling to precipitate said pure 19-norandrost-4-ene-3,17-dione or 19-norethisterone.

11. The process of claim 1, wherein said crystallization solvent is selected from the group consisting of benzene, toluene, xylene, ethylbenzene, carbon tetrachloride, chloroform, methylene dichloride, 1,2-dichloroethane, 1,1-dichloroethane, 1,1,1-trichloroethane, 1,1,2-trichloroethane, 1,1,2-trichloroethylene, 1,1,2,2-tetrachloroethane, acetone, methyl ethyl ketone, methyl isobutyl ketone, isopropyl alcohol, n-hexane, n-heptane, n-octane, and n-decane.

12. The process of claim 1, wherein in said step (c), said pure 19-norethisterone is crystallized from at least one crystallization solvent selected from the group consisting of toluene, 1,1,2-trichloroethylene and methyl isobutyl ketone.

13. The process of claim 1, wherein in said step (c), said pure 19-norandrost-4-ene-3,17-dione is crystallized from at least one crystallization solvent selected from the group consisting of toluene, 1,1,2-trichloroethylene, methyl isobutyl ketone and n-octane.

14. The process of claim 1, wherein said basic alumina has been calcined at above about 400° C.

15. The process of claim 1, wherein said basic alumina contains more than about 0.2% sodium oxide.

16. The process of claim 1, wherein said basic alumina has a particle size of from 10 to 100 mesh.

17. The process of claim 16, wherein said particle size is from 30 to 60 mesh.

18. The process of claim 1, wherein said step (b) is carried out at a temperature not higher than 70° C.

19. The process of claim 18, wherein said temperature is from 10° to 30° C.

20. The process of claim 1, wherein said step (b) is carried out at a linear velocity not greater than 5 m/hr.

21. The process of claim 20, wherein said linear velocity is not greater than 3 m/hr.

22. The process of claim 1, wherein in said step (b) after said resulting solution from step (a) has been passed through said column, the column is then washed with an additional portion of the same solvent used in step (a), the combined effluents constituting said alumina-treated solution.

* * * * *